(12) United States Patent
Tanaka et al.

(10) Patent No.: US 11,061,007 B2
(45) Date of Patent: Jul. 13, 2021

(54) WETTING TEST APPARATUS AND METHOD FOR GAS SENSOR

(71) Applicant: NGK INSULATORS, LTD., Nagoya (JP)

(72) Inventors: Jumpei Tanaka, Nagoya (JP); Tomoya Seimori, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 168 days.

(21) Appl. No.: 16/297,985

(22) Filed: Mar. 11, 2019

(65) Prior Publication Data

US 2019/0285596 A1   Sep. 19, 2019

(30) Foreign Application Priority Data

Mar. 13, 2018   (JP) ............... JP2018-045922

(51) Int. Cl.
*G01N 33/00*   (2006.01)
*G01N 13/00*   (2006.01)

(52) U.S. Cl.
CPC ........... *G01N 33/007* (2013.01); *G01N 13/00* (2013.01)

(58) Field of Classification Search
CPC ...... G01N 33/007; G01N 13/00; G01N 27/26; G01N 27/409; G01N 27/416
See application file for complete search history.

(56) References Cited

U.S. PATENT DOCUMENTS 8,360,738 B2 *   1/2013   Van Den Wyngaert .......... F04B 49/065
                                                               417/44.2
2017/0176378 A1 *   6/2017   Otjes ............... G01N 33/0037

FOREIGN PATENT DOCUMENTS

JP   2017-190968 A   10/2017

* cited by examiner

*Primary Examiner* — Brandi N Hopkins
(74) *Attorney, Agent, or Firm* — Mattingly & Malur, PC

(57) ABSTRACT

A wetting test apparatus for a gas sensor includes: a pipe having a flow path therein; a blower for allowing a gas to flow through the flow path; a water supplier for supplying moisture to the flow path; at least one gas sensor for detecting at least one component of the gas flowing through the flow path; and a pressure variation generator for generating variations in a pressure of the gas flowing through the flow path by changing an effective cross-sectional area of the flow path.

10 Claims, 8 Drawing Sheets

[FIG. 1]
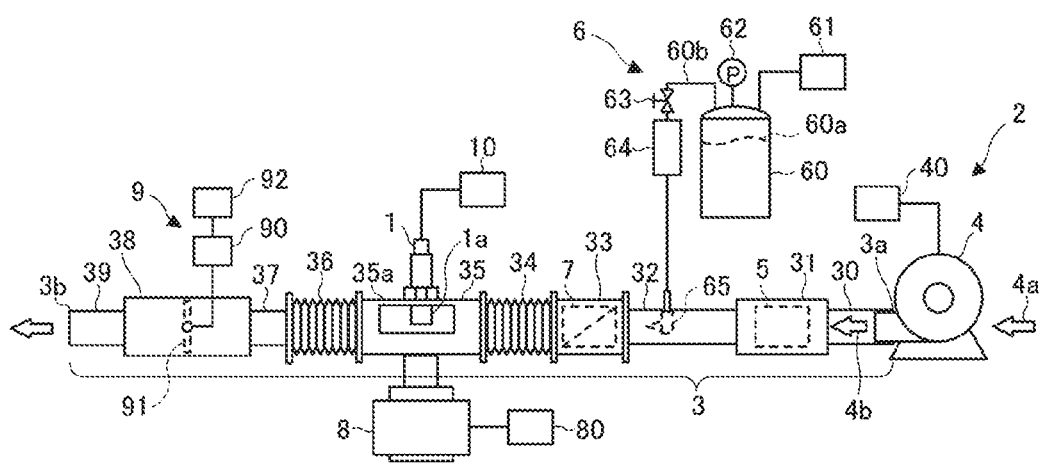

[FIG. 2]
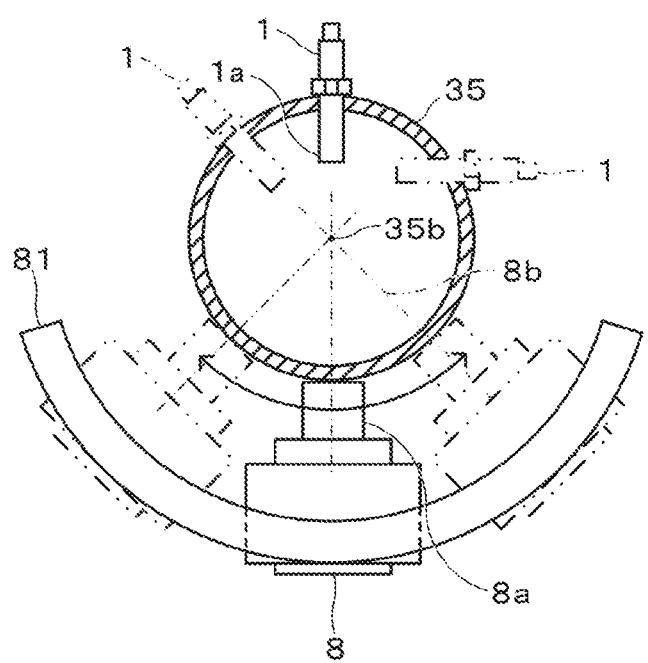

[FIG. 3]
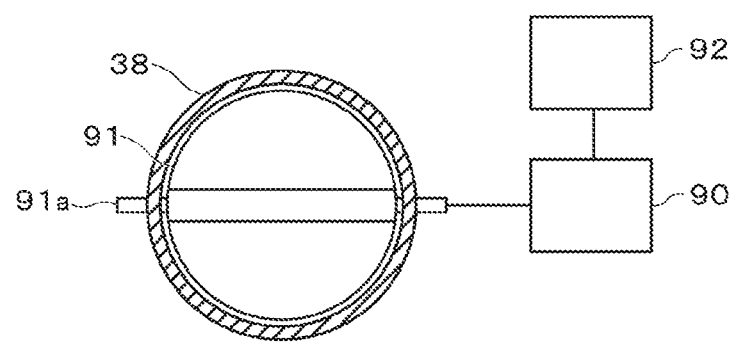

[FIG. 4]
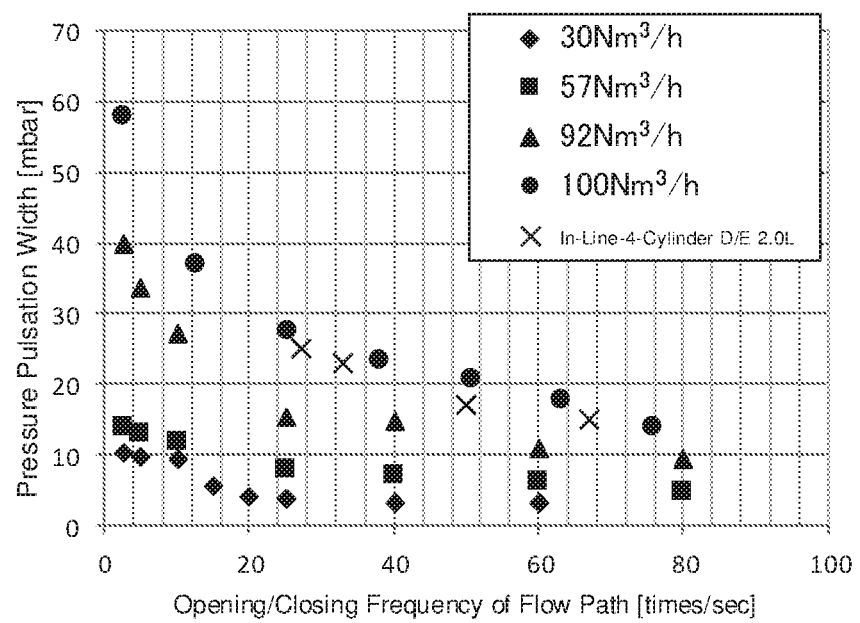

[FIG. 5]
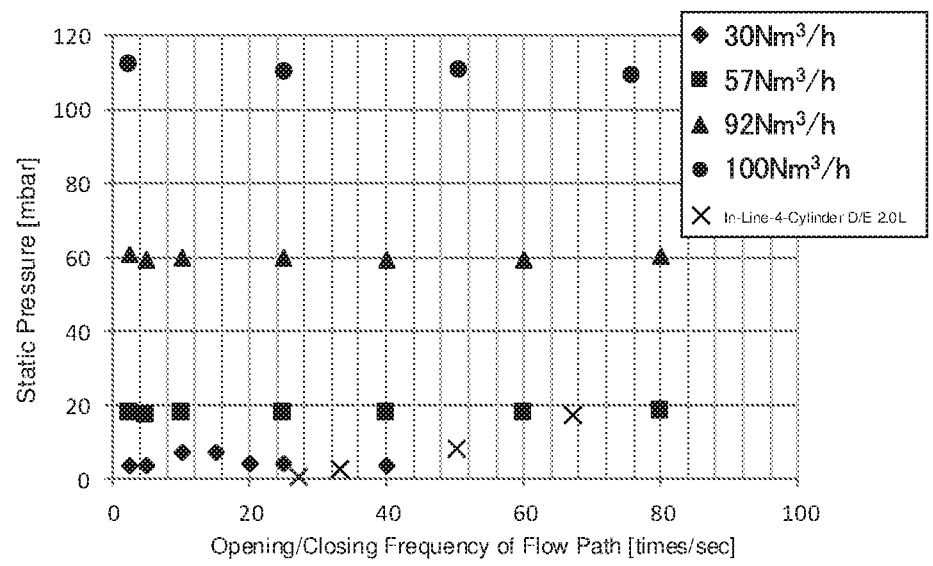

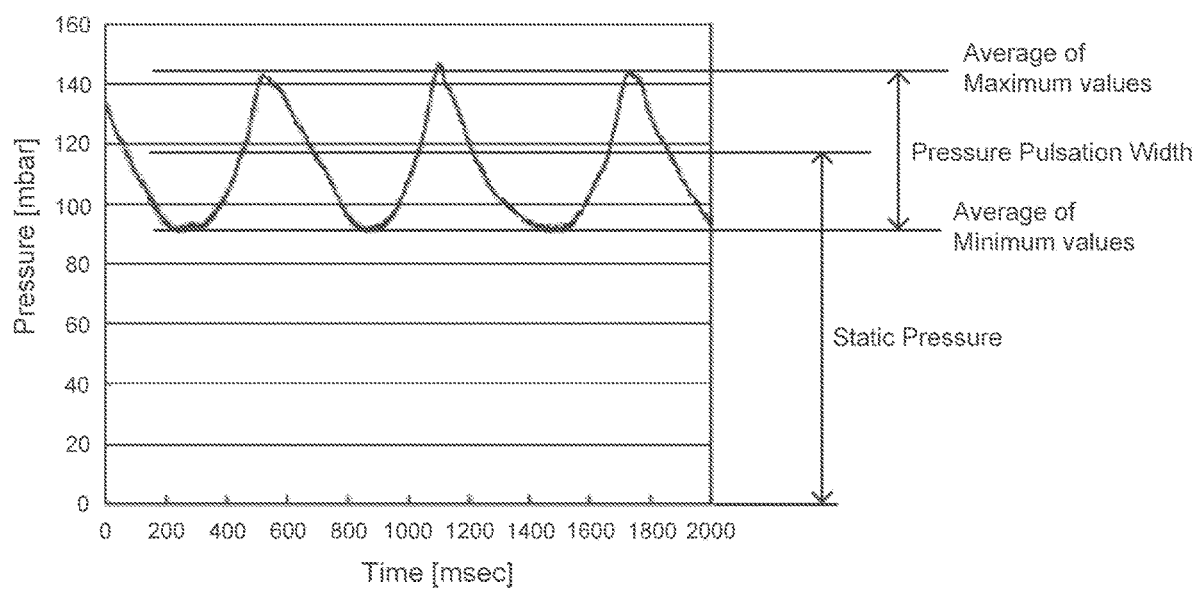

[FIG. 7]
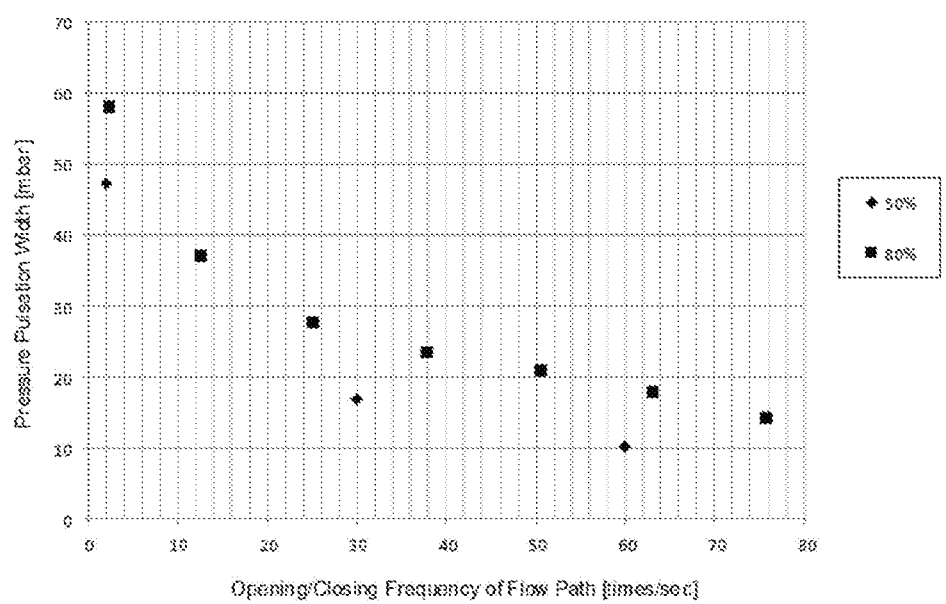

[FIG. 8]
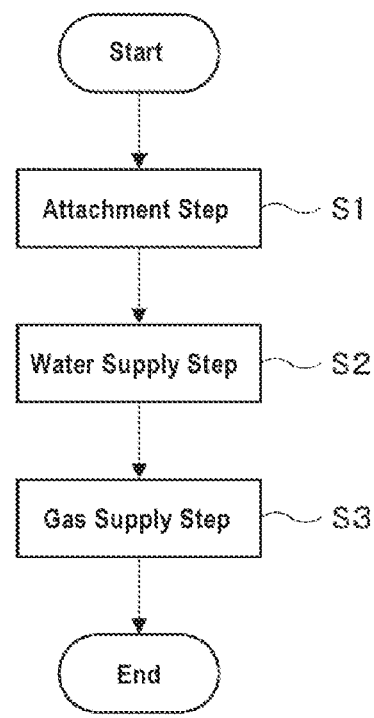

WETTING TEST APPARATUS AND METHOD FOR GAS SENSOR

CROSS-REFERENCE TO RELATED APPLICATION

The present application claims priority from Japanese application JP 2018-045922, filed on Mar. 13, 2018, the contents of which is hereby incorporated by reference into this application.

TECHNICAL FIELD

The present invention relates to a wetting test apparatus and method for gas sensor for investigating an impact of a gas sensor subjected to water.

BACKGROUND ART

As such a gas sensor wetting test apparatus which has been conventionally used, the configuration disclosed in the following Patent Document 1 and the like can be mentioned. That is, the conventional test apparatus includes an engine; an exhaust pipe through which an exhaust gas of the engine flows; and a gas sensor attached to the exhaust pipe. The engine is started after moisture adheres to an inner wall surface of the exhaust pipe by injecting misty water or steam into the exhaust pipe, and the moisture adhering to the inner wall surface of the exhaust pipe is scattered by the exhaust gas from the engine. Based on the adhesion of the scattered moisture to the gas sensor, an impact of the gas sensor subjected to water is investigated.

CITATION LIST

Patent Literature
Patent Document 1: Japanese Patent Application Publication No. 2017-190968

SUMMARY OF INVENTION

Technical Problem

In the conventional wetting test apparatus for the gas sensor as described above, since the engine is used, an impact of disturbance is significant and it is difficult to quantify the test results. Examples of the disturbance include a change of displacement due to atmospheric pressure and a change of a temperature of the exhaust gas due to the outside temperature.

The present invention has been made to solve the above problems. An object of the present invention is to provide a wetting test apparatus for a gas sensor, which can suppress the impact of disturbance and obtain more quantitative test results. Further, one of the other objects is to provide a wetting test method for a gas sensor, which can suppress the impact of disturbance and obtain more quantitative test results.

Solution to Problem

In one aspect of the present invention, a wetting test apparatus for a gas sensor includes: a pipe having a flow path therein; a blower for allowing a gas to flow through the flow path; a water supplier for supplying moisture to the flow path; at least one gas sensor for detecting at least one component of the gas flowing through the flow path; and a pressure variation generator for generating variations in a pressure of the gas flowing through the flow path by changing an effective cross-sectional area of the flow path.

Further, in one aspect of the present invention, a wetting test method for a gas sensor comprises the steps of: attaching at least one gas sensor to a pipe; supplying moisture to a flow path by a water supplier; and allowing a gas to flow through the flow path by a blower and generating variations in a pressure of the gas by a pressure variation generator to scatter the moisture in the flow path toward the gas sensor by the gas having the pressure variations.

Advantageous Effects of Invention

According to one embodiment of the wetting test apparatus and method for the gas sensor of the present invention, the pressure variation generator generates variations in a pressure of the gas flowing through the flow path, so that moisture can be scattered toward the gas sensor by a gas flow that simulates an exhaust gas from an engine. This can allow an impact of disturbance to be suppressed and more quantitative test results to be obtained.

BRIEF DESCRIPTION OF DRAWINGS

FIG. 1 is an arrangement view showing a wetting test apparatus for a gas sensor according to an embodiment of the present invention.
FIG. 2 is a front view showing a vibrator in FIG. 1.
FIG. 3 is a front view showing a pressure variation generator in FIG. 1.
FIG. 4 is a graph showing a relationship between an opening/closing frequency of a flow path by a valve body and a pressure pulsation width of a gas, when changing a flow rate of the gas from a blower in FIG. 1.
FIG. 5 is a graph showing a relationship between an opening/closing frequency of a flow path by a valve body and a static pressure of a gas, when changing a flow rate of the gas from a blower in FIG. 1.
FIG. 6 is an explanatory view showing the pressure pulsation width of the gas in FIG. 4 and the static pressure of the gas in FIG. 5.
FIG. 7 is a graph showing a relationship between an opening/closing frequency of a flow path by a valve body and a pressure pulsation width of a gas, when changing a maximum closing ratio of the flow path in FIG. 1.
FIG. 8 is a flowchart showing a wetting test method for gas sensor using the wetting test apparatus in FIG. 1.

DESCRIPTION OF THE PREFERRED EMBODIMENTS

Hereinafter, embodiments for carrying out the present invention will be described with reference to the drawings. It should be noted that the present invention is not limited to the embodiments, and it can be embodied by modifying elements without departing from the spirit of the present invention. Further, some elements may be deleted from all elements shown in the embodiments.

FIG. 1 is an arrangement view showing a wetting test apparatus 2 for a gas sensor 1 according to an embodiment of the present invention, FIG. 2 is a front view showing a vibrator 8 in FIG. 1, and FIG. 3 is a front view showing a pressure variation generator 9 in FIG. 1. The gas sensor 1 shown in the substantially center in FIG. 1 is a sensor which is mounted on a vehicle having an engine and which can detect at least one component of an exhaust gas of the vehicle. Examples of the components detected by the gas sensor 1 include NOx, HC, ammonia, oxygen and the like.

Although not shown, the gas sensor 1 includes a gas sensing element made of ceramics. When the gas sensor 1 is mounted on the vehicle, the gas sensing element of the gas sensor 1 is heated to a high temperature of about 600° C. by both of a heater contained in the gas sensor 1 and an exhaust gas. When moisture adheres to the gas sensing element at the high temperature, the gas sensing element may be cracked due to thermal shock. In particular, when the air temperature is low such as in the winter, dew condensation water accumulated in an exhaust system of the vehicle may be scattered by the exhaust gas and adhere to the gas sensor 1.

The wetting test apparatus 2 shown in FIG. 1 is an apparatus for carrying out a wetting test for checking an impact of the gas sensor 1 subjected to water while simulating a state where the gas sensor 1 is mounted on the vehicle. As shown in FIG. 1, the wetting test apparatus 2 includes: a pipe 3; a blower 4; an airflow meter 5; a water supplier 6; a honeycomb structure 7; a vibrator 8; and a pressure variation generator 9.

The pipe 3 according to the present embodiment has a flow path therein, which is communicated from an introduction end 3a shown on the right side of FIG. 1 to a discharge end 3b shown on the left side of FIG. 1. An inner diameter of the pipe 3 can be, for example, from 50 to 350 mm. The pipe 3 according to the present embodiment is structured by connecting a plurality of tubular bodies from the introduction end 3a to the discharge end 3b. That is, the pipe 3 according to the present embodiment includes: an introduction pipe 30; an airflow meter housing 31; a first connecting pipe 32; a honeycomb structure housing 33; a first flexible tube 34; a chamber 35; a second flexible tube 36; a second connecting pipe 37; a pressure variation generator housing 38; and a discharge pipe 39. These tubular bodies included in the pipe 3 can be respectively replaced with tubular bodies having other inner diameters.

The introduction pipe 30 according to the present embodiment is a tubular body provided with the introduction end 3a. The blower 4 is connected to the introduction end 3a of the introduction pipe 30. The blower 4 according to the present embodiment can be, for example, a device or the like that sucks an outside air 4a and generates a flow of a gas 4b by applying energy to the outside air 4a due to rotational motion of an impeller. The blower 4 that can be used may be, for example, a blower or the like that can flow the gas 4b having a wind speed of from 1 to 20 m/s as converted into a standard state (1 atm and 25° C.) into a flow path in the pipe 3. The blower that can be used may be, for example, other blowing means except for an engine, such as a gas cylinder in which a compressed gas is stored. The gas 4b from the blower 4 flows through the flow path in the pipe 3 from the introduction pipe 30 toward the discharge end 3b. That is, the blower 4 according to the present embodiment is disposed at the most upstream in the flow direction of the gas 4b. A blower controller 40 is connected to the blower 4. The blower controller 40 controls the blowing operation of the blower 4 so that a flow rate and/or flow velocity of the gas 4b from the blower 4 is changeable. The blower controller 40 may include an arithmetic unit for performing arithmetic processing based on a program; an inverter; and the like.

The airflow meter housing 31 according to the present embodiment is a tubular body incorporating the airflow meter 5. The airflow meter 5 is a sensor for measuring a flow rate and/or a flow velocity of the gas 4b flowing through the flow path. A measured value of the airflow meter 5 can be used for controlling the operation of the blower 4 by the blower controller 40. Further, the measured value of the airflow meter 5 can be stored in a storage device (not shown) and can be displayed on the airflow meter 5 or a display provided separately from the airflow meter 5.

The first connecting pipe 32 according to the present embodiment connects the airflow meter housing 31 to the honeycomb structure housing 33. Inside the first connecting pipe 32, a shower nozzle 65 of the water supplier 6 is inserted. The water supplier 6 according to the present embodiment supplies droplet-like moisture to the flow path through the shower nozzle 65. The water supplier 6 supplies the moisture to the flow path, thereby simulating a state where the moisture adheres to the inner side of the exhaust system of the vehicle. The water supplier 6 that can be used may be, for example, an apparatus having an ability to supply water of from 0.7 to 1.5 L/min.

The water supplier 6 according to the present embodiment includes: a tank 60; a pressurizer 61; a pressure gauge 62; an on-off valve 63; a flow meter 64; and the shower nozzle 65.

In the tank 60, water 60a is reserved.

The pressurizer 61 pressurizes the inside of the tank 60 by supplying compressed air into the tank 60.

The pressure gauge 62 measures an internal pressure of the tank 60. The pressurizing operation of the pressurizer 61 is controlled so that the internal pressure measured by the pressure gauge 62 is a predetermined value. Further, a measured value of the pressure gauge 62 can be stored in a storage device (not shown) and can be displayed on the pressure gauge 62 or a display provided separately from the pressure gauge 62.

The on-off valve 63 is provided in a supply pipe 60b to open and close the flow path in the supply pipe 60b of the tank 60. The on-off valve 63 may switch the opened and closed state of the flow path in a fully closed state or a fully opened state, or may continuously change the opening degree of the flow path. When the flow path in the supply pipe 60b is opened by the on-off valve 63, the water 60a in the pressurized tank 60 is supplied to the shower nozzle 65 through the supply pipe 60b.

The flow meter 64 can measure a flow rate of the water 60a passing through the supply pipe 60b of the tank 60. Further, the flow meter 64 can measure a cumulative flow rate of the water 60a passing through the supply pipe 60b of the tank 60. A measured value of the flow meter 64 can be used for controlling the operation of the pressurizer 61 and the on-off valve 63. The measured value of the flow meter 64 can be stored in a storage device (not shown) and can be displayed on the flowmeter 64 or a display provided separately from the flowmeter 64.

The shower nozzle 65 according to the present embodiment is a nozzle body having fine openings and supplies the water 60a as droplets supplied through the supply pipe 60b to the flow path in the pipe 3. The shower nozzle 65 can be replaced with other shower nozzles having openings of different sizes in order to change the size of the droplet from the shower nozzle 65. The shower nozzle 65 according to the present embodiment is disposed in a direction of injecting the droplets toward the downstream side in the flow direction of the gas 4b. However, the shower nozzle 65 may inject the droplets toward the upstream side in the flow direction of the gas 4b.

The honeycomb structure housing 33 according to the present embodiment is a tubular body containing the honeycomb structure 7. As well known, the honeycomb structure 7 is a pillar shaped structure in which a plurality of cells extending in the longitudinal direction of the honeycomb structure 7 are provided in a honeycomb shape. The honeycomb structure 7 can be used for purifying the exhaust gas of the vehicle. The plurality of cells are formed so as to be partitioned from each other by partition walls and penetrate from a first end face to a second end face of the honeycomb structure 7. Further, the plurality of cells forms fluid flow paths inside the honeycomb structure 7. For a material of the honeycomb structure 7, ceramics or metals can be used.

The honeycomb structure 7 according to the present embodiment is disposed on an upstream side of the gas sensor 1 (a chamber 35) in the flow direction of the gas 4b and on a downstream side of a moisture supply position (the shower nozzle 65). By disposing the honeycomb structure 7 at this position, it is possible to simulate a possible condition of an actual vehicle in which the moisture adhering to and/or penetrated in the honeycomb structure 7 is scattered toward the gas sensor 1. In particular, in the case of the ceramic honeycomb structure 7, a larger amount of moisture adheres and/or is penetrated into the honeycomb structure 7 as compared with the metal honeycomb structure 7. When it is assumed that the ceramic honeycomb structure 7 is to be mounted on the vehicle on which the gas sensor 1 is mounted, it is particularly useful that the ceramic honeycomb structure 7 is placed at that position to simulate the possible condition of the actual vehicle.

The first flexible tube 34 and the second flexible tube 36 according to the present embodiment are flexible tubular bodies. The first and second flexible tubes 34, 36 according to the present embodiment are structured by metallic bellows structural tubes. The first flexible tube 34 and the second flexible tube 36 are attached to both ends of the chamber 35. The first flexible tube 34 connects the chamber 35 to the honeycomb structure housing 33 and the second flexible tube 36 connects the chamber 35 to the second connecting pipe 37. As will be described below, the first and second flexible tubes 34, 36 absorb vibration when the vibrator 8 applies vibration to the chamber 35. As the first and second flexible tubes 34, 36 absorb vibration, the vibration transmitted to other portions of the pipe 3 are reduced.

The chamber 35 according to the present embodiment is a tubular body to which the gas sensor 1 is attached. The gas sensor 1 is attached to the chamber 35 such that a sensing portion 1a including the gas sensing element is positioned in the flow path in the pipe 3. The sensing portion 1a refers to a portion including an element exposed to the gas 4b. The chamber 35 is provided with an opening 35a to which a transparent plate material such as an acrylic resin or the like is attached. Through this opening 35a, a state of the sensing portion 1a in the chamber 35 and a scattering state of water can be confirmed from the outside. A storage device 10 for storing measured values of the gas sensor 1 is connected to the gas sensor 1. The storage device 10 may include a circuit for A/D-converting an output signal of the gas sensor 1. Further, the measured value of the gas sensor 1 can be displayed on a display (not shown).

The vibrator 8 for applying vibration to the chamber 35 is connected to the chamber 35 according to this embodiment. Examples of the vibrator 8 that can be used include an actuator having a plunger 8a that moves forward and backward along a single axis. The applying of the vibration to the chamber 35 by the vibrator 8 can allow simulation that the vibration during traveling of the vehicle such as vibrations of engine and/or vibrations due to road surface change acts on the gas sensor 1. A vibration controller 80 is connected to the vibrator 8. The vibration controller 80 controls the vibrating operation of the vibrator 8, so that at least one of the amplitude and the frequency of the vibration by the vibrator 8 is variable. The vibration controller 80 may include an arithmetic device that performs calculation processing based on a program, and an inverter, or the like.

As shown in FIG. 2, the vibrator 8 is supported by a frame body 81 extending in a circumferential direction of the chamber 35, and is guided by the frame body 81 so as to be displaceable in the circumferential direction of the chamber 35. That is, the vibrator 8 can apply not only the vibration in the vertical direction but also the vibration in a direction inclined to the vertical direction to the chamber 35. As shown in FIG. 2, it is preferable that the vibrator 8 is displaced while being tilted so that a straight line 8b along the vibration direction of the vibrator 8 passes through a central axis 35b of the chamber 35. Further, the vibrator 8 may be displaced while being tilted so that the straight line 8b along the vibration direction of the vibrator 8 passes through a straight line parallel to the central axis 35b. It should be noted that the frame body 81 is omitted in FIG. 1.

Further, as shown by two-dot chain lines in FIG. 2, the attachment position of the gas sensor 1 to the chamber 35 is also variable. The gas sensor 1 can be attached to the chamber 35 such that the longitudinal direction of the gas sensor 1 passes through the central axis 35b of the chamber 35. Further, the gas sensor 1 can be attached to the chamber 35 such that the longitudinal direction of the gas sensor 1 does not pass through the center axis 35b of the chamber 35. For example, the gas sensor 1 may be displaced during the wetting test, such as by attaching a frame body for guiding the displacement of the gas sensor 1 to a peripheral surface of the chamber 35 in a state where the gas sensor 1 is attached.

Returning now to FIG. 1, the second connecting pipe 37 according to the present embodiment connects the second flexible tube 36 to the pressure variation generator housing 38.

The pressure variation generator housing 38 according to the present embodiment is a tubular body containing a valve body 91 of the pressure variation generator 9. The pressure variation generator 9 is a device for generating variations in a pressure of the gas 4b flowing through the flow path by changing an effective cross-sectional area of the flow path. The effective cross-sectional area of the flow path refers to an area of a region where the gas 4b can flow, among inner cross sections of the pressure variation generator housing 38 when viewing the inside of the pressure variation generator housing 38 along the flow direction of the gas 4b. It is possible to simulate a situation where moisture is scattered to the gas sensor 1 by the exhaust gas from the engine whose pressure varies, by scattering moisture to the gas sensor 1 by the gas 4b whose pressure varies similarly. The pressure variation generator 9 may randomly change the effective cross-sectional area of the flow path, but it is preferable to periodically change the effective cross-sectional area of the flow path. The pressure variation generator 9 that can be used includes a device or the like which can achieve periodic pressure variation (pulsation) of from 0.1 to 250 times/second (Hz), for example.

The pressure variation generator 9 according to the present embodiment is disposed on the downstream side of the gas sensor 1 in the flow direction of the gas 4b. By disposing the pressure variation generator 9 at such a position, the gas 4b having more sharp pressure pulsation is blown to the gas sensor 1. Further, if the pressure variation generator 9 is disposed on the upstream side of the gas sensor 1, the moisture which should adhere to the gas sensor 1 may adhere to the pressure variation generator 9. However, the disposing of the pressure variation generator 9 on the downstream side of the gas sensor 1 can avoid such a risk.

As shown particularly in FIG. 3, the pressure variation generator 9 according to the present embodiment is structured by a butterfly valve having a motor 90 and a valve body 91 rotatably driven by the motor 90. A rotating shaft 91*a* of the valve body 91 is rotatably supported by the pressure variation generator housing 38. The rotation of the valve body 91 allows a periodical change of the effective cross-sectional area of the flow path. By structuring the pressure variation generator 9 by the butterfly valve, the gas 4*b* having various pressure pulsations can be more reliably obtained. A rotation controller 92 is connected to the motor 90. The rotation controller 92 controls the operation of the motor 90, whereby the changing frequency of the effective cross-sectional area (opening/closing frequency) of the flow path by the valve body 91 is variable.

The valve body 91 according to the present embodiment is structured by a plate having a size that is rotatable within the pressure variation generator housing 38. Although the valve body 91 has any outer shape, it preferably has the same shape as an inner edge of the pressure variation generator housing 38. That is, as shown in FIG. 3, when the inner edge of the pressure variation generator housing 38 is circular, the valve body 91 is preferably a circular plate.

At least one of the valve body 91 and the pressure variation generator housing 38 according to the present embodiment is replaced with another, whereby a maximum closing ratio of the flow path can be changed. The maximum closing ratio is a ratio of a maximum extending area of the valve body 91 to an inner cross-sectional area of the pressure variation generator housing 38. That is, the maximum closing ratio is expressed by: (the maximum extending area of the valve body 91/the inner cross-sectional area of the pressure variation generator housing)×100%. The inner cross-sectional area of the pressure variation generator housing 38 is an area on an inner side of the pressure variation generator housing 38 in a surface orthogonal to the longitudinal direction of the pressure variation generator housing 38. When the inner edge of the pressure variation generator housing 38 is circular, the inner cross-sectional area of the pressure variation generator housing 38 may be calculated from the inner diameter of the pressure variation generator housing 38. The maximum extending area of the valve body 91 is an area of an end face of the valve body 91 as viewing the valve body 91 along the longitudinal direction of the pressure variation generator housing 38 when the end face of the valve body 91 extends along a surface orthogonal to the longitudinal direction of the pressure variation generator housing 38. When the valve body 91 is the circular plate, the maximum extending area of the valve body 91 may be an area of the end face of the circular plate calculated from a diameter of the circular plate.

The discharge pipe 39 according to the present embodiment is a tubular body provided with a discharge end 3*b*. The discharge end 3*b* of the discharge pipe 39 is opened, and the scattered moisture is discharged together with the gas 4*b* from the discharge end 3*b*.

Next, the effect produced using the butterfly valve as the pressure variation generator 9 will be described in more detail. FIG. 4 is a graph showing a relationship between an opening/closing frequency of the flow path by the valve body 91 and a pressure pulsation width of the gas 4*b* when changing a flow rate of the gas 4*b* from the blower 4 in FIG. 1, FIG. 5 is a graph showing a relationship between the opening/closing frequency of the flow path by the valve body 91 and a static pressure of the gas 4*b* when changing the flow rate of the gas 4*b* from the blower 4 in FIG. 1, and FIG. 6 is an explanatory view showing the pressure pulsation width of the gas 4*b* in FIG. 4 and the static pressure of the gas 4*b* in FIG. 5.

The present inventors have investigated the relationship between the opening/closing frequency of the flow path by the valve body 91, and the pressure pulsation width and static pressure of the gas 4*b* while changing the flow rate of the gas 4*b* from the blower 4. The results are shown in FIGS. 4 and 5.

The horizontal axis in FIG. 4 represents the opening/closing frequency [times/sec] of the flow path by the valve body 91, and the vertical axis in FIG. 4 represents the pressure pulsation width [mbar] of the gas 4*b*. The opening/closing frequency of the flow path is the number of flow path opening/closing operations per a second (unit time), which is different from the rotational speed of the rotating shaft 91*a* of the valve body 91. Where the rotating shaft 91*a* of the valve body 91 is rotated one time per a second, the opening/closing frequency of the flow path by the valve body 91 is 2 [times/sec]. The opening/closing frequency of the flow path corresponds to a pulsation frequency of the gas 4*b*. The pressure pulsation width [mbar] of the gas 4*b* represents a difference between an average value of the minimum values and an average value of the maximum values of the pressure of the gas 4*b* as shown in FIG. 6.

Each circle plot in FIG. 4 shows a relationship between the opening/closing frequency [times/sec] of the flow path and the pressure pulsation width [mbar] when the flow rate of the gas 4*b* from the blower 4 is set to 100 $Nm^3/h$. Similarly, each triangular plot shows the relationship when the flow rate of the gas 4*b* is set to 92 $Nm^3/h$, and each square plot shows the relationship when the flow rate of the gas 4*b* is set at 57 $Nm^3/h$, and each diamond plot shows the relationship when the flow rate of the gas 4*b* is set to 30 $Nm^3/h$. Each plot of the X symbol in FIG. 4 shows a relationship between a pulsation frequency [times/sec] and a pressure pulsation width [mbar] for an exhaust gas from a 2 L in-line 4-cylinder diesel engine.

As shown in FIG. 4, it was confirmed that the pressure pulsation width of the gas 4*b* could be changed by altering the opening/closing frequency of the flow path by the valve body 91. It was also confirmed that the pressure pulsation width of the gas 4*b* could be increased as the flow rate of the gas 4*b* from the blower 4 was increased.

The horizontal axis in FIG. 5 represents an opening/closing frequency [times/sec] of the flow path by the valve body 91, and the vertical axis in FIG. 5 represents a static pressure [mbar] of the gas 4*b*. The static pressure of the gas 4*b* represents an average value of the pressures of the gas 4*b* as shown in FIG. 6.

Each circle plot in FIG. 5 shows a relationship between the opening/closing frequency [times/sec] of the flow path and the static pressure [mbar] when the flow rate of the gas 4*b* from the blower 4 is set to 100 $Nm^3/h$. Similarly, each triangular plot shows the relationship when the flow rate of the gas 4*b* is set to 92 $Nm^3/h$, and each square plot shows the relationship when the flow rate of the gas 4*b* is set at 57 $Nm^3/h$, and each diamond plot shows the relationship when the flow rate of the gas 4*b* is set to 30 $Nm^3/h$. Each plot of the X symbol in FIG. 5 shows a relationship between a pulsation frequency [times/sec] and a static pressure [mbar] for an exhaust gas from a 2 L in-line 4-cylinder diesel engine.

As shown in FIG. 5, it was confirmed that the static pressure of the gas 4*b* could be changed by altering the flow rate of the gas 4*b* from the blower 4.

Next, FIG. 7 is a graph showing a relationship between the opening/closing frequency of the flow path by the valve body 91 and the pressure pulsation width of the gas 4b when changing the maximum closing ratio of the flow path in FIG. 1. The present inventors have also investigated the relationship between the opening/closing frequency of the flow path by the valve body 91 and the pressure pulsation width of the gas 4b when changing the maximum closing ratio of the flow path. The results are shown in FIG. 7. As described above, the maximum closing ratio of the flow path can be changed by replacing at least one of the valve body 91 and the pressure variation generator housing 38 with another.

The horizontal axis in FIG. 7 represents the opening/closing frequency [times/sec] of the flow path by the valve body 91, and the vertical axis in FIG. 7 represents the pressure pulsation width [mbar] of the gas 4b. Each square plot in FIG. 7 shows a relationship between the opening/closing frequency [times/sec] of the flow path and the pressure pulsation width [mbar] when the maximum closing ratio is 80%, and each diamond plot shows the relationship when the maximum closing ratio is 50%.

As shown in FIG. 7, it was confirmed that the relationship between the opening/closing frequency [times/sec] of the flow path and the pressure pulsation width [mbar] can be adjusted by changing the maximum closing ratio of the flow path.

From the results shown in FIG. 4, FIG. 5 and FIG. 7, it will be understood that the opening/closing frequency of the flow path by the valve body 91 (the changing frequency of the effective sectional area of the flow path), the flow rate of the gas 4b from the blower 4 and the maximum closing ratio of the flow path are changed, thereby enabling the gas 4b simulating the exhaust gases of various engines to be obtained.

Next, FIG. 8 is a flow chart showing a wetting test method of the gas sensor 1 using the wetting test apparatus 2 in FIG. 1. The wetting test method according to the present embodiment includes: an attachment step (step S1); a water supply step (step S2); and an airflow (gas) supply step (step S3).

In the attaching step (step S1), the gas sensor 1 to be tested is attached to the chamber 35 of the pipe 3.

In the water supply step (step S2), the moisture is supplied to the flow path inside the pipe 3 by the water supplier 6. The supply of moisture by the water supplier 6 is performed until a predetermined amount of moisture is supplied into the flow path.

In the gas supply step (step S3), the gas 4b is allowed to flow through the flow path by the blower 4 while changing the effective cross-sectional area of the flow path by the pressure variation generator 9. When the gas 4b is allowed to flow through the flow path by the blower 4, the vibrator 8 applies vibration to the chamber 35 to which the gas sensor 1 is attached. As described above, the pressure of the gas 4b varies in accordance with a change of the effective cross-sectional area of the flow path. The moisture in the flow path is scattered toward the gas sensor 1 by the gas 4b whose pressure varies. Therefore, the moisture can be scattered toward the gas sensor 1 by the gas 4b that simulates the exhaust gas from the engine, without using the engine. As a result, the impact of disturbance can be suppressed, and more quantitative test results can be obtained. The opening/closing frequency of the flow path by the valve body 91, the flow rate of the gas 4b from the blower 4 and the closing ratio of the flow path are set to predetermined value before the start of the wetting test method, such that the gas 4b can simulate the exhaust gas in the vehicle on which the gas sensor 1 to be tested is mounted.

In the wetting test apparatus 2 for the gas sensor 1 and the wetting test method using the apparatus according to the present embodiment, the pressure variation generator 9 generates variations in a pressure of the gas 4b flowing through the flow path, so that the moisture can be scattered toward the gas sensor 1 by the flow of the gas 4b which simulates the exhaust gas from the engine without using the engine. This can allow the impact of disturbance to be suppressed, and more quantitative test results to be obtained.

Further, the pressure variation generator 9 according to the present embodiment can periodically change the effective cross-sectional area of the flow path, so that the flow of the gas 4b simulating the exhaust gas from the engine can be more reliably obtained.

Furthermore, the pressure variation generator 9 according to the present embodiment is a butterfly valve having the motor 90 and the valve body 91 rotationally driven by the motor 90, so that the flow of the gas 4b having various pressure pulsations can be more reliably obtained.

Moreover, the flow rate and/or the flow velocity of the gas 4b from the blower 4 and the changing frequency of the effective cross-sectional area of the flow path by the pressure variation generator 9 according to the present embodiment are variable, so that the flow of the gas 4b having various pressure variations can be more reliably obtained. Even if only one of the flow rate and/or the flow velocity of the gas 4b from the blower 4 and the changing frequency of the effective cross-sectional area of the flow path by the pressure variation generator 9 is changeable, the flow of the gas 4b having various pressure variations can be obtained.

Further, the pressure variation generator 9 according to the present embodiment is disposed on the downstream side of the gas sensor 1 in the flow direction of the gas 4b, so that the gas 4b having a more sharp pressure pulsation can be blown to the gas sensor 1, as well as a risk that moisture which should adhere to the gas sensor 1 will adhere to the pressure variation generator 9 can be avoided.

Furthermore, the vibrator 8 can apply vibration to the chamber 35 to which the gas sensor 1 according to the present embodiment is attached, so that the wetting test can be carried out while simulating that vibration during traveling of the vehicle acts on the gas sensor 1, thereby enabling improvement of accuracy of the wetting test.

Moreover, the flexible tubes 34, 36 are attached to both ends of the chamber 35 according to the present embodiment, so that it is possible to reduce vibrations transmitted to other portions of the pipe 3 when applying the vibrations to the chamber 35 by the vibrator 8.

Further, in the present embodiment, the honeycomb structure 7 is arranged in the flow path on the upstream side of the gas sensor 1 in the flow direction of the gas 4b and on the downstream side of the supplied position of the moisture by the water supplier 6, so that the wetting test can be carried out while simulating a possible state of an actual vehicle in which moisture adhering to or penetrated into the honeycomb structure 7 is scattered toward the gas sensor 1, thereby enabling improvement of accuracy of the wetting test. This configuration is particularly useful when it is assumed that the ceramic honeycomb structure 7 is mounted on a vehicle on which the gas sensor 1 is mounted.

In the embodiment, the pressure variation generator 9 is described as the butterfly valve. However, the pressure variation generator may open and close the flow path of the pipe by other valves such as a cylinder valve, a gate valve or a ball valve, for example. Further, the pressure variation generator may change the effective cross-sectional area of the flow path by other methods such as a method in which at least a part of the pipe is a flexible tubular body and the flexible tubular body is intermittently confined from the outside.

According to the descriptions of the embodiment, the water supplier 6 supplies moisture in the form of droplets to the flow path. However, the water supplier may supply to the flow path moisture in other forms such as water stream or steam.

Furthermore, according to the descriptions of the embodiment, one gas sensor is attached to the pipe 3 (the chamber 35). However, a plurality of gas sensors may be attached to the pipe.

DESCRIPTION OF REFERENCE NUMERALS

1 gas sensor
2 wetting test apparatus
3 pipe
4 blower
6 water supplier
7 honeycomb structure
8 vibrator
9 pressure variation generator
34, 36 flexible tube
35 chamber
90 motor
91 valve body

What is claimed is:

1. A wetting test apparatus for a gas sensor, comprising:
   a pipe having a flow path therein;
   a blower configured to cause a gas to flow through the flow path;
   a water supplier which supplies moisture to the flow path;
   at least one gas sensor which detects at least one component of the gas flowing through the flow path; and
   a pressure variation generator configured to generate variations in a pressure of the gas flowing through the flow path by changing an effective cross-sectional area of the flow path.

2. The wetting test apparatus for a gas sensor according to claim 1, wherein the pressure variation generator is configured tocan periodically change the effective cross-sectional area of the flow path.

3. The wetting test apparatus for a gas sensor according to claim 2, wherein the pressure variation generator is a butterfly valve comprising a motor and a valve body rotationally driven by the motor.

4. The wetting test apparatus for a gas sensor according to claim 2, wherein at least one of a flow rate and/or a flow velocity of the gas from the blower and a changing frequency of the effective cross-sectional area by the pressure variation generator is variable.

5. The wetting test apparatus for a gas sensor according to claim 1, wherein the pressure variation generator is disposed on a downstream side of the gas sensor in a flow direction of the gas.

6. The wetting test apparatus for a gas sensor according to claim 1, wherein the pipe comprises a chamber to which the gas sensor is attached, and the apparatus further comprises a vibrator that can apply vibration to the chamber.

7. The wetting test apparatus for a gas sensor according to claim 6, wherein the pipe further comprises flexible tubes attached to both ends of the chamber.

8. The wetting test apparatus for a gas sensor according to claim 1, wherein the apparatus further comprises a honeycomb structure disposed in the flow path on an upstream side of the gas sensor in the flow direction of the gas and on a downstream side of a supplied position of the moisture by the water supplier.

9. A wetting test method for a gas sensor using the wetting test apparatus for a gas sensor according to claim 1, the method comprising the steps of:
   attaching the at least one gas sensor to the pipe;
   supplying moisture to the flow path by the water supplier; and
   allowing a gas to flow through the flow path by the blower and generating variations in a pressure of the gas by the pressure variation generator to scatter the moisture in the flow path toward the gas sensor by the gas having the pressure variations.

10. The wetting test apparatus for a gas sensor according to claim 1, wherein the blower is disposed on an upstream side of the gas sensor in a flow direction of the gas and the pressure variation generator is disposed on a downstream side of the gas sensor in a flow direction of the gas.

* * * * *